United States Patent [19]
Yoshida et al.

[11] Patent Number: 5,841,532
[45] Date of Patent: Nov. 24, 1998

[54] METHOD FOR EVALUATING OXYGEN CONCENTRATING IN SEMICONDUCTOR SILICON SINGLE CRYSTAL

[75] Inventors: Tomosuke Yoshida, Annaka; Yutaka Kitagawara, Takasaki, both of Japan

[73] Assignee: Shin-Etsu Handotai Co., Ltd., Tokyo, Japan

[21] Appl. No.: 800,393

[22] Filed: Feb. 14, 1997

[30] Foreign Application Priority Data

Feb. 22, 1996 [JP] Japan .................................. 8-059967

[51] Int. Cl.$^6$ ........................................ G01N 21/64
[52] U.S. Cl. ........................................ 356/318; 356/300
[58] Field of Search ................................ 356/300, 318

[56] References Cited

U.S. PATENT DOCUMENTS 4,429,047  1/1984  Jastrzebski et al. .

FOREIGN PATENT DOCUMENTS 3-033642  2/1991  Japan .

OTHER PUBLICATIONS

Y. Kitagawara, et al., "Evaluation of Oxygen Precipitated Silicon Crystals by Deep–Level Photoluminescence at Room Temperature and Its Mapping", Journal of the Electrochemical Society, Aug. 1992, vol. 139, No. 8, pp. 2277–2281.

K. Terashima, et al., "Photoluminescence of Ring–Distribution of Oxygen Precipitates in Czochralski Silicon", Materials Science Forum, 1995, vol. 196–201, pp. 1129–1134.

M. Nakamura, et al., "Photoluminescence Measurement of Carbon in Silicon Crystal Irradiated with High Energy Electrons", Journal of the Electrochemical Society, Dec. 1994, vol. 141, No. 12, pp. 3576–3580.

M. Tajima, "Infrared Microscopic Photoluminescence Mapping on Semiconductors at Low–Temperatures", Institute of Physics Conference Series, 1996, vol. 149, pp. 243–249.

*Primary Examiner*—Vincent P. McGraw
*Attorney, Agent, or Firm*—Oliff & Berridge, PLC

[57] ABSTRACT

A method and apparatus for evaluating an oxygen concentration in a semiconductor silicon single crystal highly doped with boron at a low cost with a high sensitivity and high reproducibility. The single crystal, which is doped with boron of a high concentration of $10^{17}$ atoms/cm$^3$ or higher, is irradiated with a light having a greater energy than that of bandgap of the semiconductor silicon while holding the single crystal at a temperature of room temperature to 50 K and photoluminescence intensities in the vicinity of a photon energy of 0.96 eV of a photoluminescence spectrum emitted from the single crystal under the above irradiation are measured to evaluate an oxygen concentration in the single crystal.

16 Claims, 6 Drawing Sheets

METHOD FOR EVALUATING OXYGEN CONCENTRATING IN SEMICONDUCTOR SILICON SINGLE CRYSTAL

BACKGROUND OF THE INVENTION

1. Field of the Invention

The present invention generally relates to a method for evaluating a semiconductor single crystal. Particularly the present invention relates to a method and apparatus suitable for evaluating an oxygen concentration in a semiconductor wafer. More particularly the present invention relates to a method and apparatus for determining an oxygen concentration in a semiconductor silicon single crystal doped with boron, as dopant, of a high concentration.

2. Related Art

Heretofore, a method based on optical absorption measurements have been widely used as one for evaluating an oxygen concentration in the bulk of a semiconductor silicon single crystal. According to the principle of the method, oxygen in the bulk of silicon single crystal is detected and quantified by measuring absorbance of incident light on the wafer caused by oxygen in interstitial lattice sites of silicon single crystal. An amount of the absorbance of light is very sensitive to a concentration of oxygen atoms occupying interstitial lattice sites in the bulk of silicon single crystal and make it possible to evaluate the concentration of oxygen atoms with a high sensitivity and high reliability. In a case where light is hard to transmit a specimen, however, the evaluation is not possible. For example, when silicon single crystal is doped with boron, as dopant, of a concentration higher than $10^{17}$ atoms/cm$^3$, or specifically higher than $10^{18}$ atoms/cm$^3$, abundant free carriers present in the bulk of the specimen almost completely absorb the incident light. Such a method as to be based on optical absorption measurements cannot absolutely apply to such doped silicon single crystal.

There have been known Charged Particle Activation Analysis method (for short CPAA method), Gas Fusion analysis method (for short GFA method) and Secondary-Ion Mass Spectrometry (for short SIMS method) as methods for measuring an oxygen concentration in silicon single crystal doped with a high concentration, for example $10^{17}$ atoms/cm$^3$ or higher, or specifically $10^{18}$ atoms/cm$^3$ or higher. In a CPAA method, a specimen is irradiated with accelerated charged particles to activate oxygen atoms in the bulk and radiation emitted from the specimen is measured to determine the concentration of oxygen atoms included in it. The method needs a cyclotron to generate accelerated charged particles. The applications are so limited as to use only in laboratories of special research institutes and cannot be suitable for use as an industrial in-line evaluation method due to the hazardous nature intrinsic to an activation analysis.

According to a GFA method, a specimen is fused in high temperature to gasify oxygen fixed in a crystal as CO and $CO_2$ and then these gases are chemically analyzed to determine the quantity of oxygen included in the specimen. A SIMS method is to measure secondary ions generated by sputtering a specimen with an ion beam under high vacuum by means of a mass spectrometer.

The above-mentioned GFA method is a fully destructive method which needs fusion of a specimen, though there are advantages that it uses a comparatively non-expensive apparatus and can be performed in a short time by a person not much skilled in the method. That the method is fully destructive means that a second evaluation of the same specimen, which becomes often required for a reason, is absolutely impossible, since the specimen is subjected to fusion. That is to say, the method has disadvantage that it cannot apply directly to a product itself and in other words, a specimen have to be specially provided for the evaluation purpose only other than products, which becomes a problem in quality assurance and which is a big loss in terms of production cost from the view point of a producer.

A GFA method has another disadvantage with respect to spatial resolution of measurements over a specimen. A specimen is cut into a plurality of near-square chips as test samples having a side of, generally, 2 mm to 10 mm, which size are selected based on requirements, firstly to perform a chemical analysis of gas with a sensitivity enough for the evaluation purpose and, secondly to secure enough accuracy by measuring a plurality of test samples extracted from the same product for evaluation use, wherein it is meaningless to prepare one test sample having a large size and analyze it, since the method is poor in reproducibility of measurement. Since sizes of such test samples are with several mm in the length of a side, there is a limitation in a distance between adjacent measuring points, which is at the lowest on the order of mm.

A SIMS method is a mass spectrometry and any element can be analyzed by selection of kinds of ion which is used for irradiation of a specimen. Detection sensitivities for elements are high and moreover, it has a high spatial resolution capability in the bulk of the specimen, since a measuring area is narrow. Against the above-mentioned advantages, the method has disadvantages, however, that firstly it needs an expensive apparatus, secondly the operational conditions of the apparatus such as degree of vacuum have to be kept in good order through measurement and thirdly it takes a lengthy time for measurement of one sample. As another disadvantage to be added, it is the same as a GFA method in that test samples with a side of several mm is needed and it is basically a destructive evaluation method.

SUMMARY OF THE INVENTION

The present invention has been made to solve such faults of the traditional methods, as mentioned above. Objects of the present invention are, accordingly, to provide a method and apparatus for evaluating an oxygen concentration in semiconductor silicon single crystal with a low cost, a high sensitivity and a high reproducibility, which crystal is doped with boron of a high concentration of $10^{17}$ atoms/cm$^3$ or higher, or specifically $10^{18}$ atoms/cm$^3$ or higher. A third and fourth objects are to provide a method and apparatus for evaluating a distribution of oxygen concentration in semiconductor silicon single crystal with a low cost, a high sensitivity and a high reproducibility, which crystal is doped with boron of the high concentrations.

A first aspect of the present invention relates to a method for evaluating an oxygen concentration in semiconductor silicon single crystal, wherein semiconductor silicon single crystal doped with boron of a concentration of $10^{17}$ atoms/cm$^3$ or higher is irradiated with a light having a greater energy than that of bandgap of the semiconductor silicon which causes the transition of electrons across the band gap to give rise to pairs of electron and hole, some of the electron-hole pairs then recombine by being captured at a site to emit photoluminescence having photon energies in the vicinity of 0.96 eV and a spectrum of such photoluminescence from the single crystal is measured.

As mentioned above, an oxygen concentration in the bulk of silicon single crystal can be measured by means of a photoluminescence method, which crystal is doped with boron of a high concentration, with accuracy and simplicity, and without destruction of a test sample, when an intensity of photoluminescence having a special energy of photon is measured, wherein influence of boron with a high concentration present in the crystal is excluded.

A second aspect of the present invention relates to the method according to the first aspect and has a feature that the spectrum of photoluminescence emitted from a semiconductor sample in the photon energy range of 0.98 eV to 0.96 eV is measured.

According to the second aspect, an oxygen concentration in silicon single crystal can be correctly measured by measuring intensities of photoluminescence in the vicinity of a photon energy of 0.96 eV, or specifically in the range of 0.98 eV to 0.96 eV.

A third aspect of the present invention relates to any of the methods according to the first and second aspects and has a feature that the measurement of photoluminescence intensity is conducted at a temperature in the range of room temperature to 50 K.

A measurement on a sample at a temperature as low as room temperature or lower purports to exclude influence of environmental temperatures and besides, to improve accuracy of measurement by increasing emission efficiency of photoluminescence in the vicinity of a photon energy of 0.96 eV.

A fourth aspect of the present invention relates to any of the methods according to the first and second aspects and has a feature that the measurement of photoluminescence intensity is conducted at a temperature in the range of 150 K to 50 K.

When a measurement of photoluminescence intensity is conducted at a temperature of a sample in the range of 150 K to 50 K, influences of environmental temperatures on measurement is excluded, emission efficiency of photoluminescence emitted in the vicinity of 0.96 eV is increased and cooling of the sample in the range of temperature is especially easy to secure by using liquid nitrogen, so that the correct measurement is achieved.

A fifth aspect of the present invention relates to any of the methods according to the first to the fourth aspects and has a feature that the measurement of photoluminescence intensity is conducted on a sample which has been subjected to a heat treatment at a temperature in the range of 400° C. to 500° C. for a time period of 1 hour to 48 hours.

When the heat treatment is applied to a semiconductor single crystal sample at a temperature in the range of 400° C. to 500° C. for a time period of 1 hour to 48 hours, oxygen atoms in the bulk of the sample gather into agglomerates dispersed with homogeneity and thereby influence on measurement of different thermal histories for different locations in the bulk of the sample is excluded, so that measurements can be conducted with higher accuracy A sixth aspect of the present invention relates to any of the methods according to the first to the fifth aspects and has a feature that a semiconductor sample is irradiated with a light having a greater energy than that of bandgap of the semiconductor silicon in such a fashion that a light beam is scanned across the surface of the sample, so that a two-dimensional distribution of oxygen concentration in the sample is obtained.

By means of the present invention, as mentioned above, a beam is scanned on the surface of the sample and thereby, detailed two-dimensional distribution of oxygen concentration in the sample can be measured, which distribution cannot be achieved by means of a gas fusion method and the like.

A seventh aspect of the present invention relates to an apparatus for evaluating a semiconductor single crystal on an oxygen concentration included therein, which apparatus comprises: means for keeping a sample from the single crystal at a temperature in the range of room temperature to 50 K; means for irradiating the sample with a light having a greater energy than that of bandgap of the semiconductor silicon while the sample is kept at a temperature in the range; and means for evaluating spectral information on intensities of photoluminescence in the vicinity of a photon energy of 0.96 eV emitted from the sample in order to determine an oxygen concentration in the sample.

A eighth aspect of the present invention relates to the apparatus according to the seventh aspect and has a feature that the apparatus further comprises means for two-dimensionally scanning with the light beam across the surface of the sample.

When the methods according to the first to sixth aspects are performed with the apparatuses according to the seventh and eighth aspects, an oxygen concentration and its distribution in the bulk of a silicon single crystal doped with boron of a high concentration are correctly evaluated with a low cost and simplicity.

The inventors has made the present invention as the result of a research in which they tried to obtain any information on oxygen in the bulk of a silicon single crystal doped with boron of a high concentration by means of a method theoretically different from the traditional methods. Heretofore, it has been known that when oxygen atoms in the bulk of a silicon single crystal are agglomerated to a certain extent, they form a deep level in the crystal and also that photoluminescence caused by the deep levels can be actually observed in a silicon single crystal lightly doped with boron (a resistivity of about 10 Ωcm) by means of a photoluminescence method (hereafter referred to as a PL method). It has been also a general understanding that in the case of a silicon single crystal having a resistivity of several Ωcm or higher, however, photoluminescence at the deep level is almost no way observed in the as-grown state because of oxygen atoms not being agglomerated so much in the bulk and that a heat treatment designed for agglomeration of oxygen atoms in the bulk is needed for making photoluminescence at the deep level observable.

The inventors of the present invention has found the presence of not a little amount of agglomerates of oxygen atoms in the bulk of an as-grown silicon single crystal when being doped with boron of a high concentration, as the result of a variety of investigations in the course of the research. Such a discovery encouraged the inventors to have an idea that even an as-grown silicon single crystal highly doped with boron would have deep-level photoluminescence which is observable by means of a PL method, even when a special heat treatment is not given the crystal for agglomeration of oxygen atoms in the bulk. The inventors have further investigated into a variety of measuring conditions and as the result, have, for the first time, found actually the deep-level photoluminescence in the vicinity of a photon energy of 0.96 eV, or specifically in the range between 0.98 eV and 0.96 eV emitted from an asgrown silicon single crystal highly doped with boron, which is observable by means of a PL method in a lower excitation intensity condition under laser irradiation, as compared with application of an ordinary PL method, and which is caused by oxygen in the bulk of the crystal. The inventors have also, for the first time, found that there is a good positive correlation between emission intensity of photoluminescence at such a deep level as to emit with a photon energy in the vicinity of 0.96 eV, or in the range of 0.98 eV to 0.96 eV and oxygen concentrations in the crystal.

The above mentioned faults of the traditional methods can be solved by the use of measurement of the deep level photoluminescence which has been, for the first time, discovered by the inventors. An oxygen concentration in a silicon single crystal highly doped with boron is easily determined only by relating to a calibration curve prepared from respective intensities of the deep-level photoluminescence measured at known oxygen concentrations in silicon single crystal specimens highly doped with boron. Such a method using the deep-level photoluminescence (hereinafter referred to as the deep-level PL method) basically is a non-destructive method and thereby makes it possible to evaluate a wafer as product itself, which can be repeated on the same wafer. With the deep-level photoluminescence method, the method shows a very high spatial resolution in measurement due to its smallness of a measuring spot in the case of evaluation of a distribution of oxygen concentration on the surface of a wafer and an apparatus for executing the method can be extended in capability so as to have a mapping function to obtain two-dimensional distributions of oxygen on the surface of a wafer.

BRIEF DESCRIPTION OF THE DRAWINGS

The novel features which are considered characteristic of the present invention are set forth with particularity in the appended claims. The present invention itself, however, and additional objects and advantages thereof will best be understood from the following description of embodiments thereof when read in connection with the accompanying drawings, in which:

DETAILED DESCRIPTION OF THE INVENTION

Below, description will be in depth given about preferred examples embodying the present invention in reference to accompanying drawings.

Figure 1:
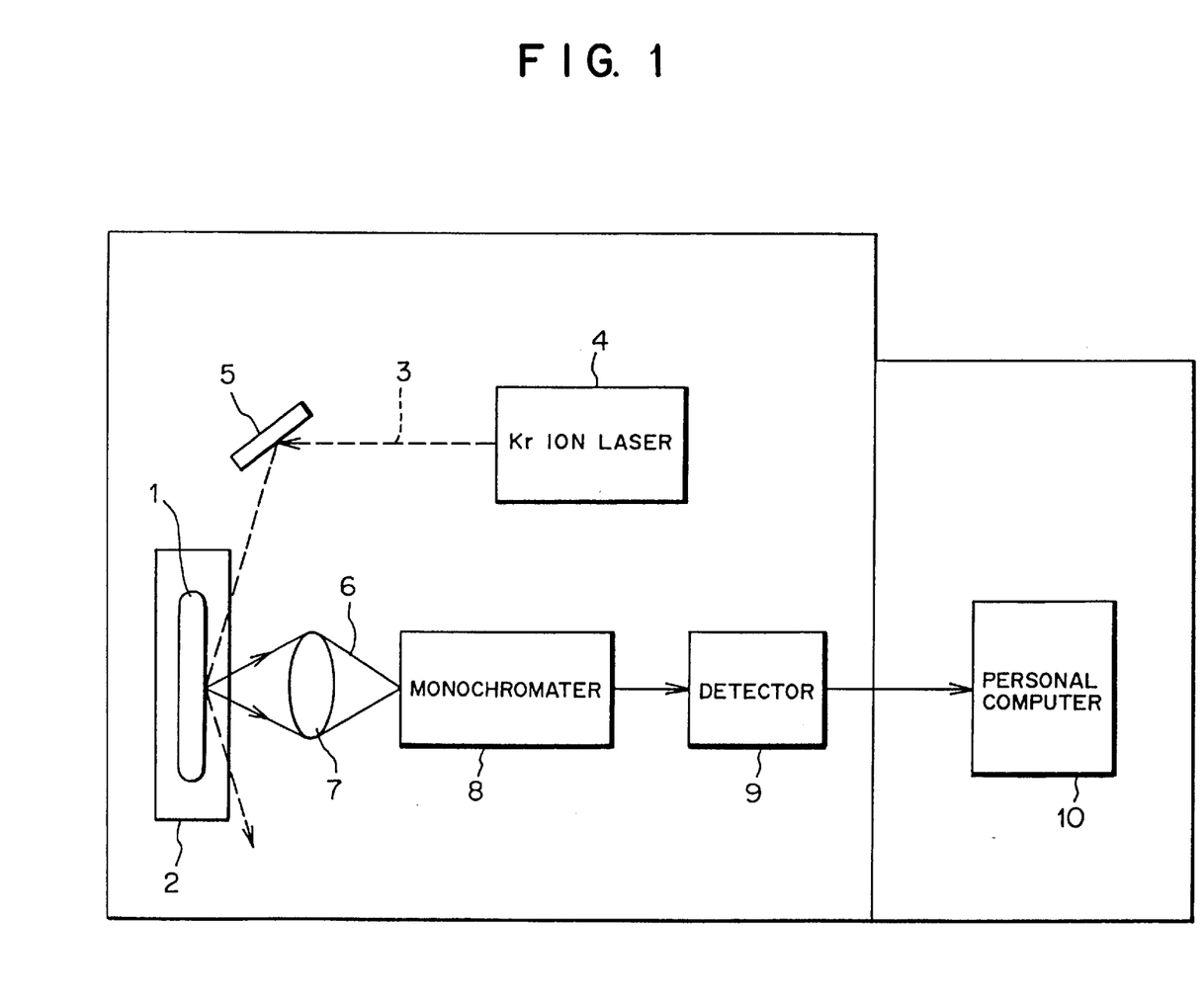
FIG. 1 is a schematic diagram showing a basic construction of a measuring apparatus according to the present invention.

FIG. 1 is a schematic diagram showing a basic construction of a measuring apparatus of photoluminescence according to the present invention. In the apparatus, a semiconductor silicon single crystal 1, which is a test specimen, is placed in a vessel 2, temperature of which is controllable in the range of room temperature to 50 K. The specimen should be kept at low temperature, or preferably at a temperature in the range of 150 K to 50 K with liquid nitrogen as coolant, since environmental influences on the measurement is excluded and emission efficiency of photoluminescence in the vicinity of a photon energy of 0.96 eV is increased for an improved accuracy in measurement. A light for excitation 3 preferably is one of a wavelength of 647 nm emitted from a Kr ion laser 4, with which light the semiconductor silicon single crystal 1 is irradiated by way of a mirror 5. An intensity of an excitation light is preferably in the range of 0.1 mW/mm$\phi$ to 500 mW/mm$\phi$ on the surface of the specimen. Agglomerates of oxygen atoms in the surface region generate photoluminescence 6 in the vicinity of a photon energy of 0.96 eV, or specifically in the range of 0.98 eV to 0.96 eV. The beams of such photoluminescence 6 are condensed by a lens 7 and then pass through a monochromator 8 to select a light of a specific wavelength, which light is then detected by a detector 9. Signals generated based on the detected light are sent to a personal computer 10 to analyze them.

In the case where an oxygen distribution on a surface of semiconductor silicon single crystal is measured, all that has to be done is to additionally install a two-dimensional scanning means (not shown), for example an X-Y table, on the side of the vessel 2 or on the side of a light source. It is preferable that a measuring surface of the specimen is either a polished surface processed by a mechano-chemical polishing or a etched surface mirror-finished by chemical etching in order to eliminate influences of surface conditions of the specimen on measurement.

Figure 2:
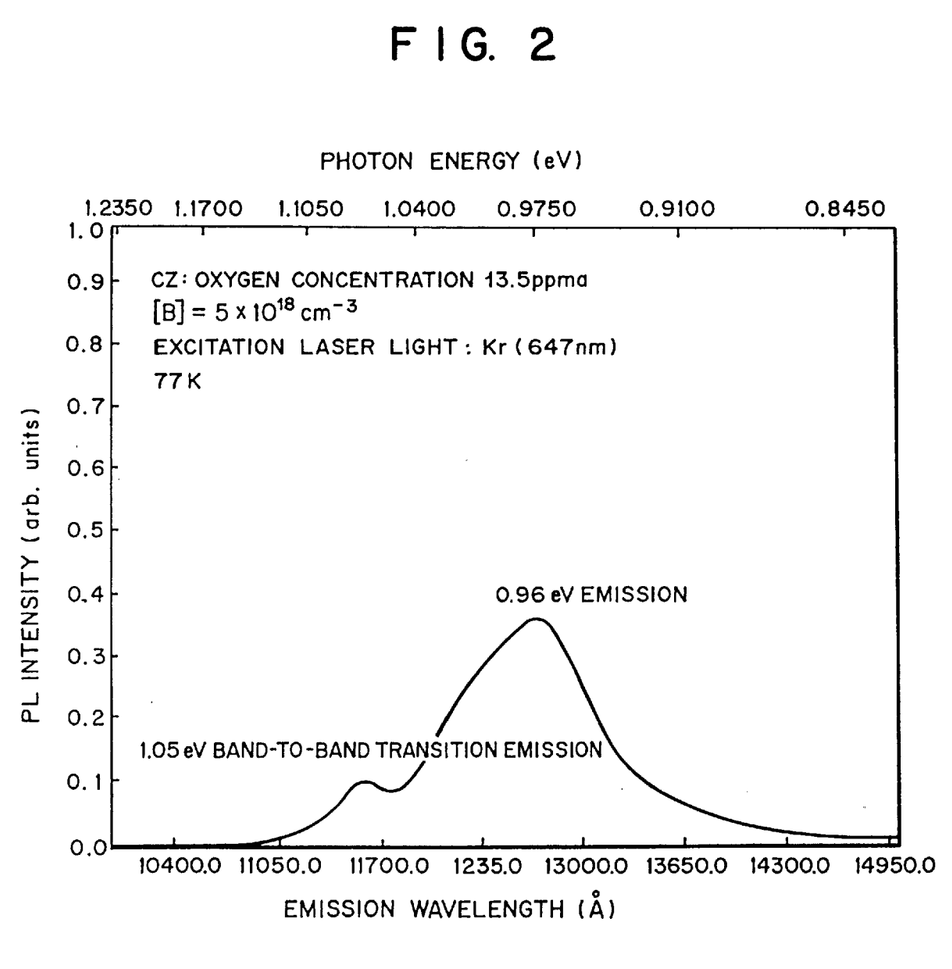
FIG. 2 is a chart depicting a photoluminescence spectrum showing an intensity-peak relating to the present invention.

FIG. 2 is a chart showing the results of measurement on a photoluminescence intensity spectrum, for which the apparatus shown in FIG. 1 is used, in the vicinity of the deep-level photoluminescence from a specimen, which has an oxygen concentration of 13.5 ppma according to JEIDA (used as the unit of oxygen concentration in the following description) and is doped with boron of a concentration of $5 \times 10^{18}$ atoms/cm$^3$, at the boiling point of liquid nitrogen, when a light of a wavelength of 647 nm emitted from a Kr ion laser is used for irradiation for excitation. Photoluminescence based on the band-to-band transition at a photon energy of 1.05 eV is observed in addition to the spectral peak at a photon energy of 0.96 eV in the spectrum, which peak the inventor has found.

As seen from the graph shown in FIG. 2, an oxygen concentration in the specimen can be determined by measuring photoluminescence intensities in the vicinity of 0.96 eV, or specifically in the range of 0.98 eV to 0.96 eV.

The following examples should be considered as exemplary of the present invention:

EXAMPLE 1

Figure 3:
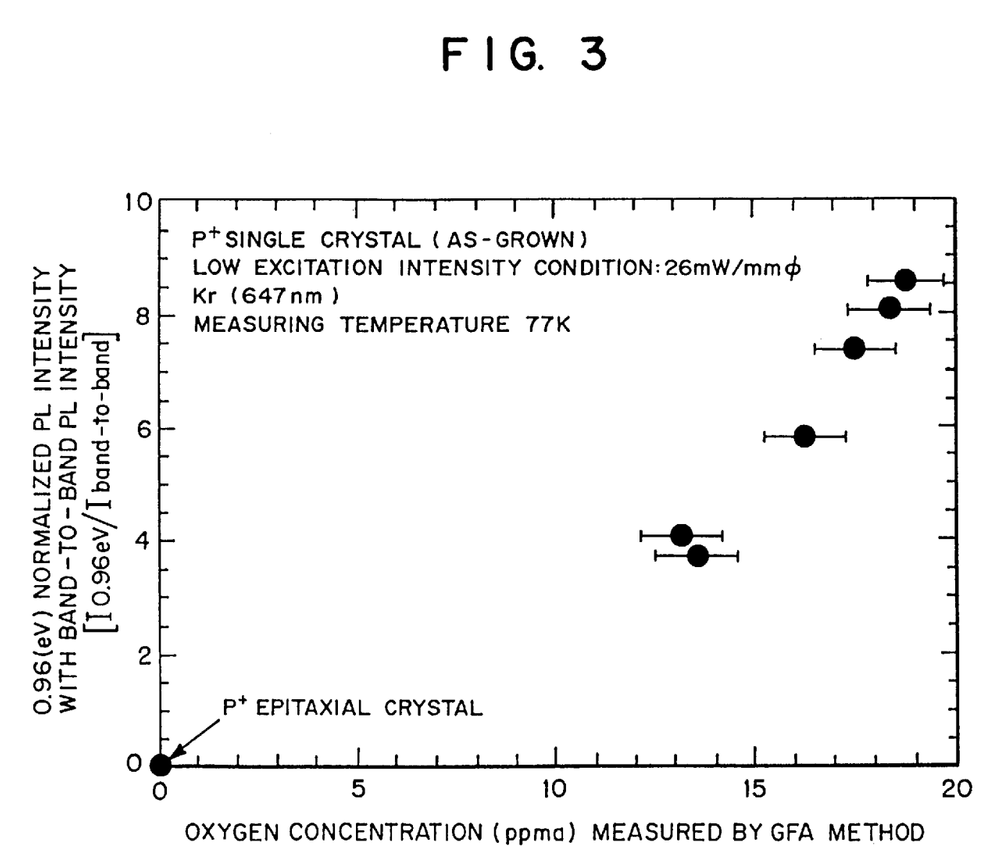
FIG. 3 is a graph showing a correlation between normalized intensities of deep-level photoluminescence and oxygen concentrations measured by means of a GFA method.

Test samples for respective measurements by means of a PL method and a GFA method were cut from respective portions in the neighborhood of the growth axis at almost the same shoulder positions lengthwise in the growth direction of six silicon single crystals grown by a Czochralski method, said crystals being all doped with boron of the same concentration of $5 \times 10^{18}$ atoms/cm$^3$ and being prepared with oxygen concentrations of six different levels for the different crystals. These test samples were divided into ten pieces respectively. Photoluminescence intensities at a photon energy of 0.96 eV were measured on five pieces from each test sample at the boiling point of nitrogen under irradiation of an excitation light having a wavelength of 647 nm emitted from a Kr ion laser, and oxygen concentrations by the GFA method were measured on the other five pieces from each test sample. The results are shown in FIG. 3, wherein normalized photoluminescence intensities from the five pieces of a test sample, which normalization was made by dividing a measured photoluminescence intensity with a band-to-band photoluminescence intensity, were plotted against an average and a pair of a maximum and minimum of oxygen concentrations from the other five pieces from each test sample, the normalized photoluminescence intensity and the average and the pair of a maximum and minimum of oxygen concentrations being displayed respectively along an ordinate axis and along an abscissa axis. The normalization has a purpose to eliminate dispersions in measurement of photoluminescence intensities under influence of various surface conditions of the measurement pieces when they are plotted as a function of oxygen concentrations. In the graph, measurements on an epitaxial layer with essentially no interstitial oxygen atom therein and doped with boron of a concentration of $5 \times 10^{18}$ atoms/cm$^3$ by both methods were also plotted for a comparison purpose. As can be seen from FIG. 3, respective sets of measurements measured by the PL method and the GFA method have a good correlation to each other. In the graph in FIG. 3, maximum and minimum values of photoluminescence intensities on the five pieces of each test sample are centralized within the width of a plotting dot due to good reproducibility of measurement, but in the case of the GFA method, a difference between the maximum and minimum values is clearly discernible and measured by as large as about 2 ppma.

EXAMPLE 2

Figure 4:
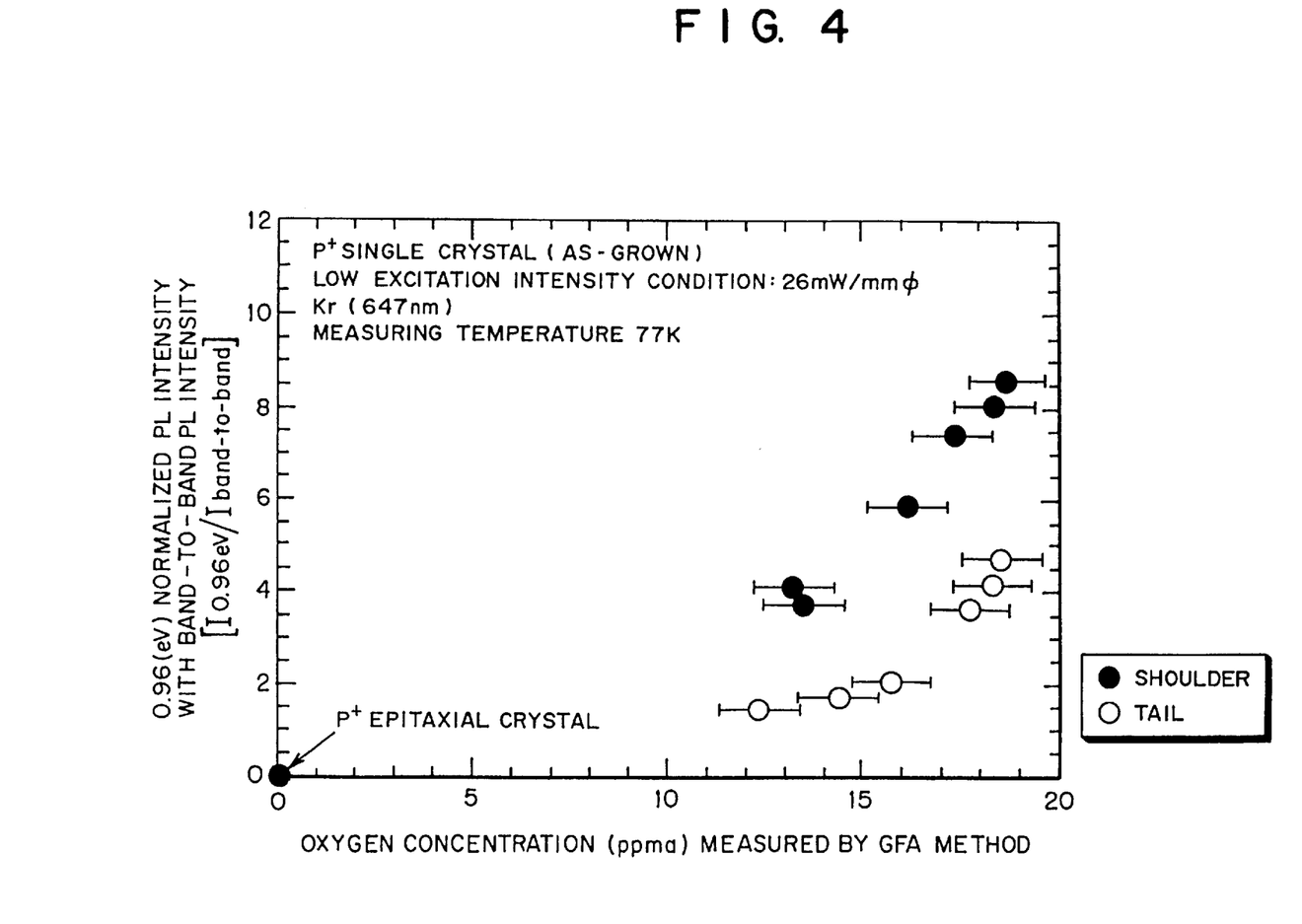
FIG. 4 is a graph showing a correlation between normalized intensities of deep-level photoluminescence and oxygen concentrations measured by means of a GFA method and respective reproducibilities in measurement of both methods.

Test samples for respective measurements by means of a PL method and a GFA method were cut from respective portions in the neighborhood of the growth axis at the same tail positions lengthwise in the growth direction of the six silicon single crystals of the example 1. These test samples were also divided into ten pieces respectively. As conducted in the example 1, not only photoluminescence intensities were measured on five pieces of each test sample, but also oxygen concentrations were measured on the other five pieces of each test sample. The results are shown together with the results obtained in the example 1 in the same way in FIG. 4 under the same normalizing condition applied to each measurement of photoluminescence intensity of each test sample. Shoulder portions and tail portions of the single crystals show different behaviors in correlation of measurement between both methods, which can be reasoned that agglomeration of oxygen atoms are different in density between the different portions of shoulder and tail, even though interstitial oxygen concentrations are the same as each other.

EXAMPLE 3

The pieces on which photoluminescence intensities had been measured in the examples 1 and 2 and additional two pieces picked up among the rest of the samples already prepared in the examples 1 and 2 were subjected to a heat treatment in a nitrogen atmosphere at 450° C. for 12 hours and then photoluminescence intensities on the pieces were measured in the same way as the example 1. Besides the photoluminescence intensities, oxygen concentrations of the additional two pieces were measured by the GFA method.

Figure 5:
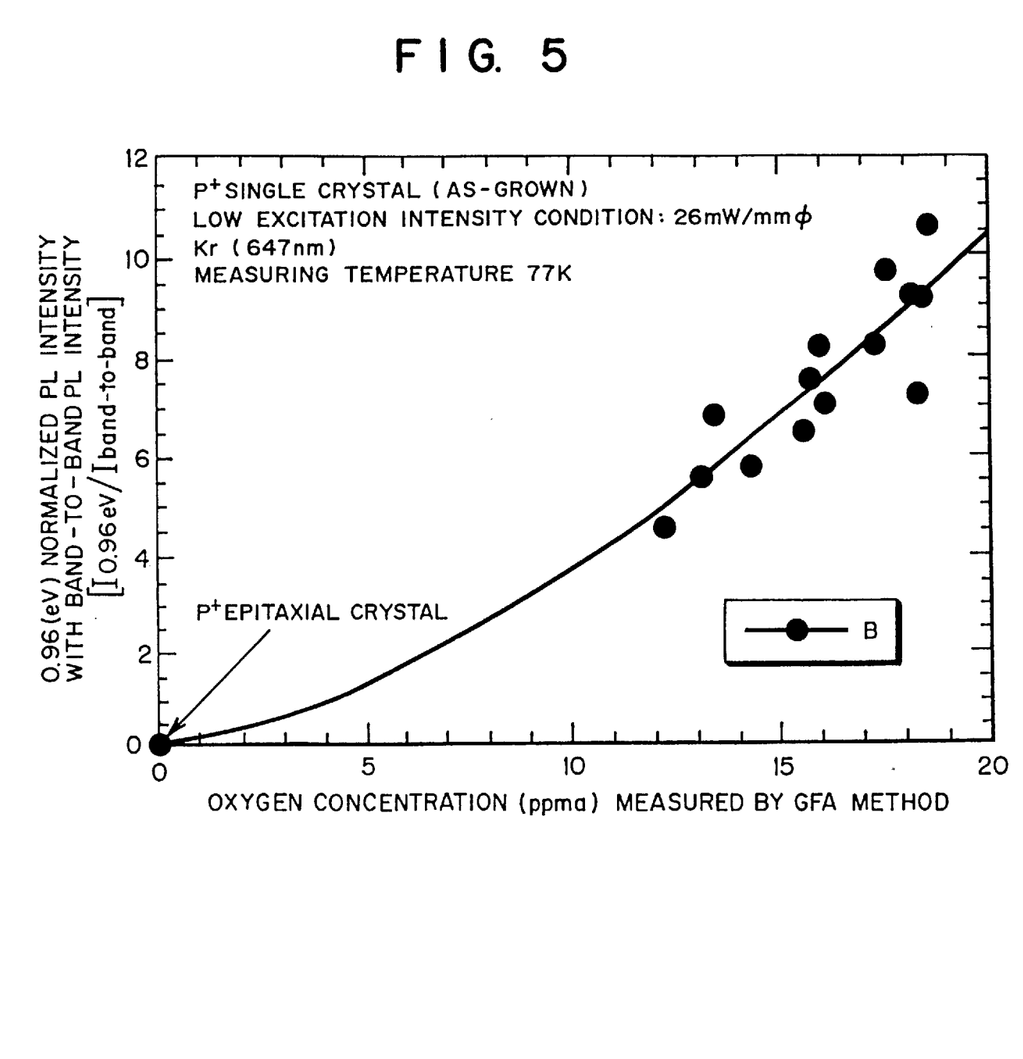
FIG. 5 is a graph showing a correlation between normalized intensities of deep-level photoluminescence and oxygen concentrations measured by means of a GFA method, which graph is to illustrate a heat treatment effect.

The results are shown in FIG. 5, wherein measured photoluminescence intensities were normalized with the band-to-band photoluminescence intensity in order to eliminate influences of various surface conditions of the measurement pieces, and each of such normalized photoluminescence intensities on the pieces was respectively plotted as a function of an average oxygen concentration measured in the examples 1 and 2 on the set of five pieces from each of the corresponding test samples, said both kinds of measurements being respectively displayed along an ordinate axis and an abscissa. As seen from the graph in FIG. 5, correlations in measurement of both methods observed from two groups of data respectively obtained from two lengthwise different positions of crystals are plotted in good coincidence with each other after the heat treatment in contrast to the different behavior observed in FIG. 4.

Such stable good correlations as seen in the above test samples after the heat treatment is seemingly derived from the facts that when test samples are subjected to a heat treatment at a temperature between 400° C. to 500° C., oxygen atoms in the bulk becomes agglomerated homogeneously in terms of a density of agglomerates and consequently difference between thermal histories received in portions of a single crystal at different lengthwise positions in the growth direction are removed, so that lengthwise differences of tested positions give no influence on correlations between both methods. It has been well known that a heat treatment of a silicon single crystal at 400° C. to 500° C. can realize homogeneous agglomeration of oxygen atoms in the bulk. Forms of agglomerates and agglomeration degrees of oxygen atoms in a silicon single crystal after a heat treatment at a temperature in the above range are preferable conditions for measurement of photoluminescence intensities as a characteristic of test samples because of a high intensity of a spectral peak and a spectrum in an orderly form. A time period for such a heat treatment is preferably in the range of one hour or more and a time period more than 48 hours is useless because of no advancement of further agglomeration and thereby simply being costly with no additional effect when longer.

EXAMPLE 4

Figure 6:
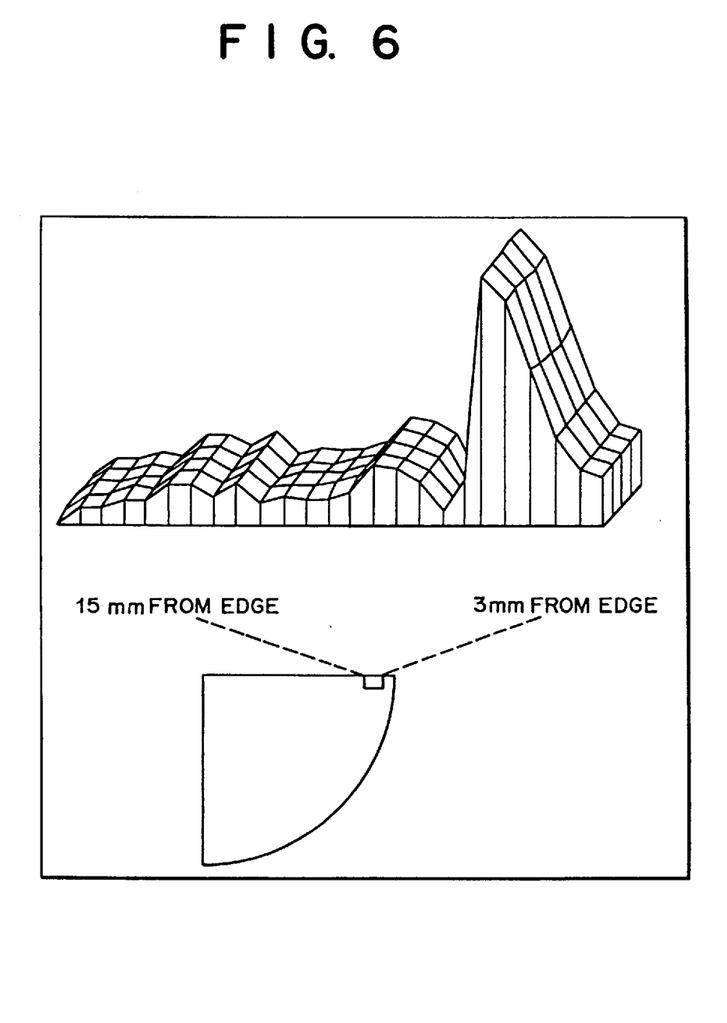
FIG. 6 is a graph showing a distribution on a surface of intensities of deep-level photoluminescence according to the present invention.

One of the test sample already used in the example 1 were cut to prepare a special test sample from the peripheral portion thereof, the length in a diameter direction of which was ranged from 3 mm to 15 mm from the peripheral edge, and photoluminescence intensities were measured on the samples at points lined up along the same diameter direction with an increment in distance of 0.5 mm. The results are shown in FIG. 6, in which a peak is observed at the outermost points in the peripheral portion, wherein measurements of oxygen concentration by a GFA method cannot be applied to the peripheral portion, because the GFA method requires, for example, a test sample in the form of a near-square having a side of several mm.

The present invention is not restricted to the above mentioned descriptions in the examples. It should be strictly understood that the examples are presented for the purpose of illustration only and any modifications which have essentially the same constituents in combination as the technical concepts recited in the claims of the present invention with the same functions and effects as those of the present invention are included in the prosecutable scope of the present invention.

As mentioned above, according to the present invention, an interstitial oxygen concentration in a semiconductor silicon single crystal highly doped with boron can be measured at a low cost with a high reproducibility and a high sensitivity, and a distribution of oxygen concentration on a surface can also be evaluated.

We claim:

1. A method for evaluating a semiconductor silicon single crystal, which is doped with boron of a concentration of $10^{17}$ atoms/cm$^3$ or higher, in regard to oxygen concentration therein, which comprises the following steps of:

irradiating a test sample from the single crystal with a light having a greater energy than that of bandgap of the semiconductor silicon; and measuring a spectrum of photoluminescence intensity in the vicinity of a photon energy of 0.96 eV which is emitted from the sample.

2. A method for evaluating a semiconductor silicon single crystal as claimed in claim 1, wherein said measuring a spectrum of photoluminescence intensity is carried out on the test sample at a temperature in the range of room temperature to 50 K.

3. A method for evaluating a semiconductor silicon single crystal as claimed in claim 1, wherein said measuring a spectrum of photoluminescence intensity is carried out on the sample at a temperature in the range of 150 K to 50 K.

4. A method for evaluating a semiconductor silicon single crystal as claimed in claim 1, wherein the test sample is irradiated with a light having a greater energy than that of bandgap of the semiconductor silicon in a scanning fashion on the surface of the sample and thereby a two-dimensional distribution on the surface of oxygen concentration is obtained.

5. A method for evaluating a semiconductor silicon single crystal, which is doped with boron of a concentration of $10^{17}$ atoms/cm$^3$ or higher, in regard to oxygen concentration therein, which comprises the following steps of:

irradiating a test sample from the single crystal with a light having a greater energy than that of bandgap of the semiconductor silicon; and measuring a spectrum of photoluminescence intensity in the range of 0.98 eV to 0.96 eV in photon energy which is emitted from the sample.

6. A method for evaluating a semiconductor silicon single crystal as claimed in claim 5, wherein said measuring a spectrum of photoluminescence intensity is carried out on the test sample at a temperature in the range of room temperature to 50 K.

7. A method for evaluating a semiconductor silicon single crystal as claimed in claim 5, wherein said measuring a spectrum of photoluminescence intensity is carried out on the sample at a temperature in the range of 150 K to 50 K.

8. A method for evaluating a semiconductor silicon single crystal as claimed in claim 5, wherein the test sample is irradiated with a light having a greater energy than that of bandgap of the semiconductor silicon in a scanning fashion on the surface of the sample and thereby a two-dimensional distribution on the surface of oxygen concentration is obtained.

9. A method for evaluating a semiconductor silicon single crystal, which is doped with boron of a concentration of $10^{17}$ atoms/cm$^3$ or higher, in regard to oxygen concentration therein, which comprises the following steps of:

giving a heat treatment to a test sample at a temperature in the range of 400° C. and 500° C. for a time period in the range of one to 48 hours;

irradiating the test sample from the single crystal with a light having a greater energy than that of bandgap of the semiconductor silicon; and measuring a spectrum of photoluminescence intensity in the vicinity of a photon energy of 0.96 eV which is emitted from the sample.

10. A method for evaluating a semiconductor silicon single crystal as claimed in claim 9, wherein said measuring a spectrum of photoluminescence intensity is carried out on the test sample at a temperature in the range of room temperature to 50 K.

11. A method for evaluating a semiconductor silicon single crystal as claimed in claim 9, wherein said measuring a spectrum of photoluminescence intensity is carried out on the sample at a temperature in the range of 150 K to 50 K.

12. A method for evaluating a semiconductor silicon single crystal as claimed in claim 9, wherein the test sample is irradiated with a light having a greater energy than that of bandgap of the semiconductor silicon in a scanning fashion on the surface of the sample and thereby a two-dimensional distribution on the surface of oxygen concentration is obtained.

13. A method for evaluating a semiconductor silicon single crystal, which is doped with boron of a concentration of $10^{17}$ atoms/cm$^3$ or higher, in regard to oxygen concentration therein, which comprises the following steps of:

giving a heat treatment to a test sample at a temperature in the range of 400° C. and 500° C. for a time period in the range of one to 48 hours;

irradiating the test sample from the single crystal with a light having a greater energy than that of bandgap of the semiconductor silicon; and measuring a spectrum of photoluminescence intensity in the range of 0.98 eV to 0.96 eV in photon energy which is emitted from the sample.

14. A method for evaluating a semiconductor silicon single crystal as claimed in claim 13 wherein said measuring a spectrum of photoluminescence intensity is carried out on the test sample at a temperature in the range of room temperature to 50 K.

15. A method for evaluating a semiconductor silicon single crystal as claimed in claim 13, wherein said measuring a spectrum of photoluminescence intensity is carried out on the sample at a temperature in the range of 150 K to 50 K.

16. A method for evaluating a semiconductor silicon single crystal as claimed in claim 13, wherein the test sample is irradiated with a light having a greater energy than that of bandgap of the semiconductor silicon in a scanning fashion on the surface of the sample and thereby a two-dimensional distribution on the surface of oxygen concentration is obtained.

* * * * *